(12) United States Patent
Moore et al.

(10) Patent No.: US 6,420,722 B2
(45) Date of Patent: Jul. 16, 2002

(54) METHOD FOR SAMPLE SEPARATION AND LIFT-OUT WITH ONE CUT

(75) Inventors: Thomas M. Moore; Rocky D. Kruger; Cheryl Hartfield, all of Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 09/863,571

(22) Filed: May 23, 2001

Related U.S. Application Data

(60) Provisional application No. 60/206,188, filed on May 22, 2000.

(51) Int. Cl.$^7$ ............................................. G01N 21/86
(52) U.S. Cl. ........................ 250/559.27; 250/559.33; 250/309
(58) Field of Search ..................... 250/548, 559.27, 250/559.3, 559.33, 221, 306, 307, 309, 492.2, 492.3

(56) References Cited

U.S. PATENT DOCUMENTS

| | | | |
|---|---|---|---|
| 4,939,364 A | 7/1990 | Ishitani et al. | 250/309 |
| 5,093,572 A | 3/1992 | Hosono | 250/310 |
| 5,171,717 A | * 12/1992 | Broom et al. | 437/226 |
| 5,270,552 A | 12/1993 | Ohnishi et al. | 250/307 |

FOREIGN PATENT DOCUMENTS

| EP | 0927880 | 7/1999 |
|---|---|---|

OTHER PUBLICATIONS

Ishitani, T., et al., "Simple Calculation on Topography of Focused–Ion–Beam Sputtered Surface", Japanese J. of Applied Physics Part 2–Letters, vol. 28, No. 2, Feb. 1989, pp. L320–L322. Japan.

Ishitani, T., et al., "Proposal for Device Transplantation using a Focused Ion Beam", Japanese J. of Applied Physics Part 2–Letters, vol. 29, No. 1, Jan. 1990, pp. L188–L190. Japan.

Ishitani, T., et al., "Micromachining and Device Transplantation Using Focused Ion Beam", Japanese J. of applied Physics Part 1–Regular Papers Short Notes & Review Papers, vol. 29, No. 10, Oct. 1990, pp. 2283–2287. Japan.

Herlinger, L. R., et al., "TEM Sample Preparation Using A Focused Ion Beam and A Probe Manipulator", Proceedings of the 22nd International Symposium for Testing and Failure Analysis, Nov. 18–22, 1996, Los Angeles, California.

Morris, S., et al., "A Technique for Preparing TEM Cross Sections to a Specific Area Using the FIB," ISTFA '91: The 17th International Symposium for Testing & Failure Analysis, Los Angeles, California, USA/ Nov. 11–15, 1991.

Szot, J., et al., "Focused ion beam micromachining for transmission electron microscopy specimen preparation of semiconductor laser diodes," J. Vac. Sci. Technol. B 10(2), Mar./Apr. 1992.

Ishitani, T., et al., "Focused–ion–beam "cutter" and "attacher" for micromachining and device transplantation," J. Vac. Sci. Technol. B 9(5), Sep./Oct. 1991.

(List continued on next page.)

Primary Examiner—Que T. Le
(74) Attorney, Agent, or Firm—John A. Thomas (57) ABSTRACT

When a desired portion is separated from an integrated circuit chip or a semiconductor wafer, the portion is separated so that the resulting sample can be moved to a location for examination by TEM, SEM or other means. A sample portion of the chip or wafer containing an area of interest is separated with a single cut by a focused ion-beam. Prior to separation, the sample is fixed to a micromanipulator probe. The sample is moved by the probe to the location for examination and fixed there. The probe is then detached from the sample by the focused ion-beam.

16 Claims, 6 Drawing Sheets

OTHER PUBLICATIONS

Yamaguchi, A., et al., "Transmission electron microscopy specimen preparation technique using focused ion beam fabrication: Application to GaAs metal–semiconductor field effect transistors," J. Vac. Sci. Technol. B 11(6), Nov./Dec. 1993.

Nikawa, K., "Applications of focused ion beam technique to failure analysis of very large scale integrations: A review," J. Vac. Sci. Technol. B 9(5), Sep./Oct. 1991.

Overwijk, M., et al., "Novel scheme for the preparation of transmission electron microscopy specimens with a focused ion beam," J. Vac. Sci. Technol. B 11(6), Nov./Dec. 1993.

Young, R.J., et al., "High–Yield and High–Throughput TEM Sample Preparation Using Focused Ion Beam Automation", Proceedings of the 24th International Symposium for Testing and Failure Analysis, Nov. 15–19, 1998, Dallas, Texas.

* cited by examiner

METHOD FOR SAMPLE SEPARATION AND LIFT-OUT WITH ONE CUT

CLAIM FOR PRIORITY

This application claims the priority of the U.S. Provisional Application filed May 22, 2000 under serial number 60/206,188 and bearing the same title.

BACKGROUND OF THE INVENTION

The present invention relates to a method for separating a sample and a method for preparing the separated sample for analysis, in cases where analysis is desired; and particularly relates to a method for separating a minute sample region from a substrate such as a semiconductor wafer.

This application describes embodiments in which a sample is cut out of a semiconductor wafer or other object by use of a focused ion beam ("FIB") and analyzed, if desired, through a transmission electron microscope ("TEM"), or by other means.

In a conventional method for TEM sample preparation, a chip, or ribbon, having a length of several mm and a width of 100–500 μm is cut out from a semiconductor integrated circuit wafer by use of a diamond wafering saw. The chip is mounted on a standard TEM grid. Then the chip is formed into a thin sample (typically 50 μm) by the FIB. The thin film sample is irradiated with an electron beam and observed by use of the TEM.

In conventional TEM observations a sample is thinned by polishing, while being observed. With this method, it is difficult to set the place of observation and direction of the sample desirably and precisely. It is necessary to carry out a step in which a region having a length of several mm and a width of 100–500 μm, and including a portion to be analyzed, is mechanically separated from the chip of an integrated circuit or semiconductor wafer. When a wafer is a sample substrate, it is necessary to divide the wafer for observation. It is difficult to process a sample to have a thickness less than 100 μm through mechanical processing by means of a diamond wafering saw or the like, because it is difficult to maintain accuracy and avoid damage. Portions which could not be cut to be thin enough through mechanical processing, would then have to be thinned with the FIB, which adds to processing time.

In another conventional method, the sample is cleaved first. The plane of cleavage is then observed by a scanning-electron microscope. This method however, makes it difficult to specify a desired portion precisely, and makes it difficult to observe the section cleaved. All of the foregoing conventional techniques have disadvantages because it is difficult to make a section even substantially flat and parallel to the sample surface for observation, and it is impossible to observe, for example, a horizontal section of a contact hole.

Another conventional method uses the FIB to cut a sample from a wafer by cutting the sample from at least two different angles after a probe has been attached to the sample. The probe then removes the sample for analysis. This method has the disadvantage that the wafer must be moved to a second angle for the second cut to be effected. These techniques typically rely on a break in electrical conductivity or trial and error to tell when the sample is isolated.

There is a need for a method of sample separation which can produce precise samples, but which does not need multiple cuts. There is a particular need for a sample-separation method which will allow the operator to see the operation in process and to clearly see when the sample separates, without the need for electrical contact tests, or the like.

SUMMARY OF THE INVENTION

The invention is a method for sample separation and lift-out within a FIB instrument. The preferred embodiment comprises the steps of, first, cleaving a wafer, having an area of interest, or target, to be removed, so as to place the target near the edge of the cleaved wafer.

Then, the tip of a micromanipulator probe is fixed to the wafer by ion-beam metal deposition. The FIB ion-beam is positioned at an angle of approximately 50 degrees to the plane of the wafer, and the ion beam cuts a U-shaped path on the surface of the wafer, so that the path surrounds the target and the fixed probe, and completely released the sample from the wafer. Next, the stage of the FIB is lowered slightly, so that the wafer is lowered beneath the released sample, now attached to the probe.

The probe with the sample fixed to it is moved to a TEM grid. The TEM grid is preferably cut across its plane so as to provide a V-shape open above. The opening allows easy access to the V-shape for placement of the sample and further operations with the ion beam. The sample is then fixed to the TEM grid by ion-beam metal deposition, and the probe is then cut by the ion-beam and detached from the fixed sample. The sample may now be thinned by the ion beam for TEM inspection, or inspected by other means. The reader should note that with the method just described, only one ion-beam cut at one angle is necessary to release the sample from the wafer and allow it to be lifted out.

DETAILED DESCRIPTION OF THE PREFERRED EMBODIMENTS

Figure 1:
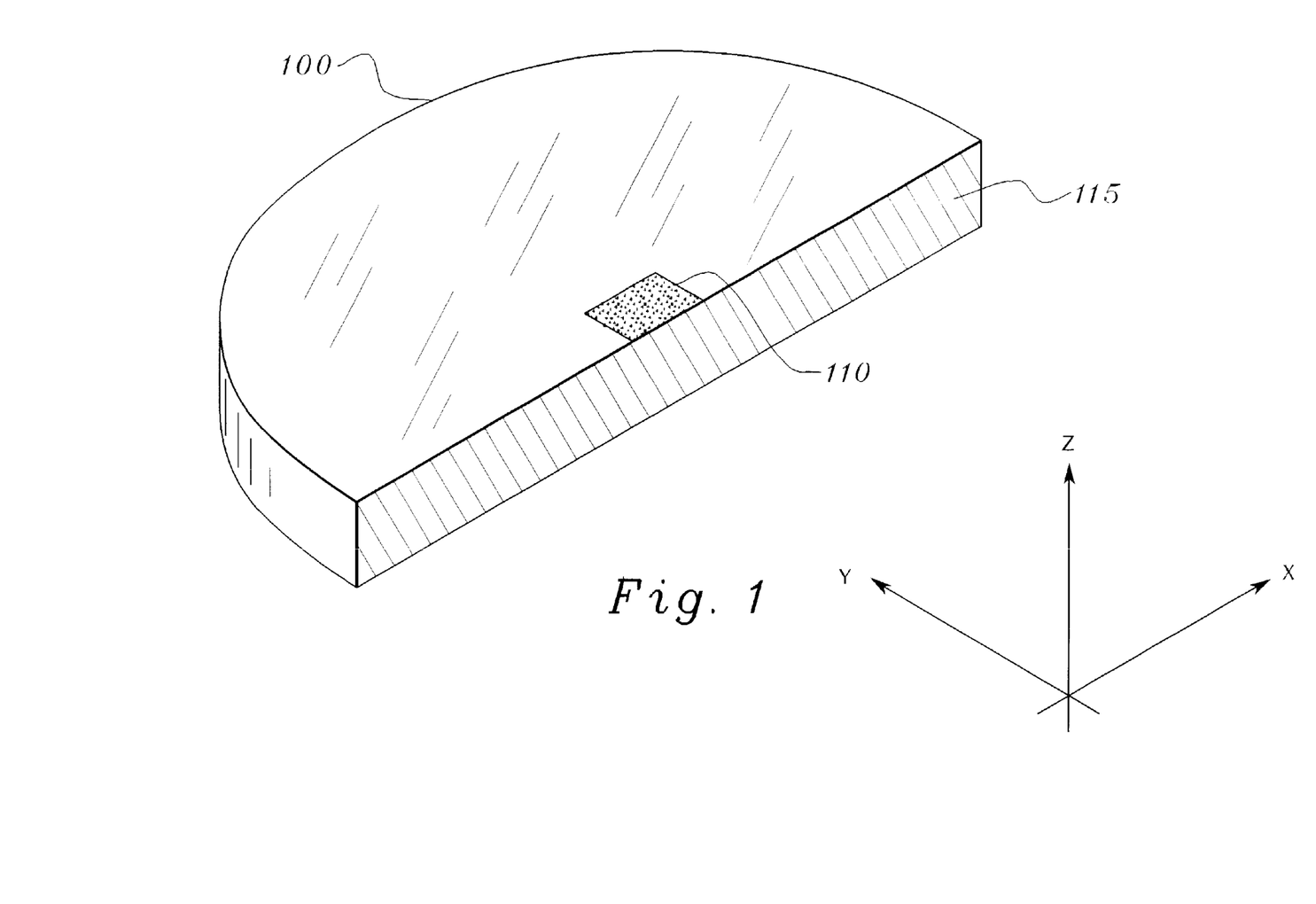
FIG. 1 is a typical wafer with an area of interest shown. The wafer is cut to create an edge near the area of interest.

FIG. 1 shows a semiconductor wafer (100) which has been cleaved or sawed so the area of interest or "target" (110) for lift-out is located as close as possible to newly formed edge (115). "Cleaving" may be done by sawing. The further from the edge, the longer (in y direction) and the deeper (in z direction), is the cut required to remove the sample. A longer and deeper cut will significantly add time to the operation. The operator inserts the wafer in FIB. In this application, we describe the object under examination as a "wafer." The "wafer" (100) need not be a semiconductor device. It may, for example be a micromechanical device, or any substance whatever requiring TEM or SEM analysis, such as particles, granules, biological materials, or thin films. The FIB may be either a single-beam model, or a dual-beam model. Typical FIB instruments are those manufactured by FEI Company of Hillsboro, Oreg., as models 200, 820, 830, or 835.

After the cleaved wafer (100) is placed in the FIB instrument, the eucentric position of the ion beam (160) should be set on the target (110). The sample should rest at an angle a depicted in FIG. 3 to the ion beam (160). The angle α can be any angle less than ninety degrees to the plane of the wafer (100), although an angle of 45–60 degrees is preferable. Typically, the wafer (100) will be perpendicular to the electron beam, if the FIB has an electron beam in addition to the ion beam (160).

Figure 2:
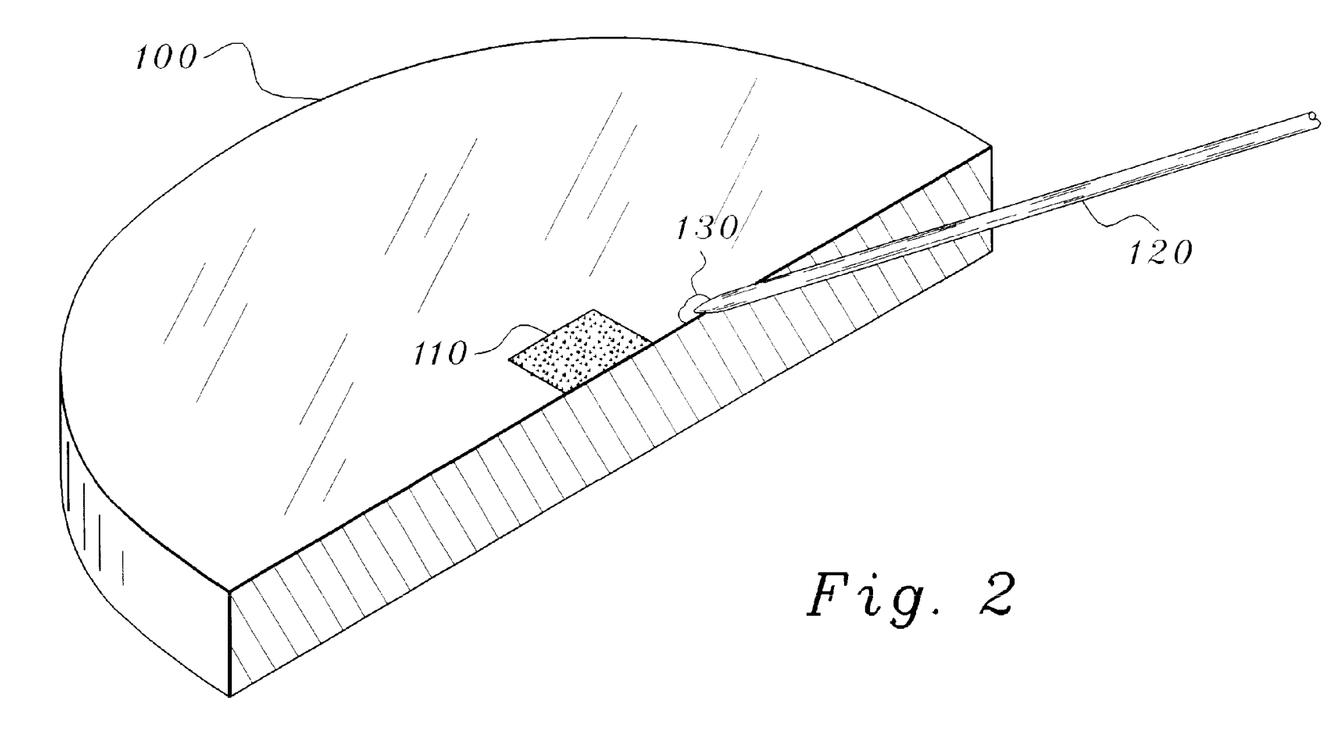
FIG. 2 shows the attachment of a probe to the wafer.

FIG. 2 shows a probe (120) that has made contact with the wafer (100) near the target (110). The probe (120) is a component of a conventional micro-manipulator tool which is attached to the FIB instrument with vacuum feed-through. A typical such micro-manipulator tool is the Model 100 by Omniprobe, Inc. of Dallas, Tex. The probe (120) is moved until its tip makes physical contact with the wafer (100), as shown in FIG. 2. The operator then preferably uses ion-beam metal deposition to form a weld (130) that fixes the tip of the probe (120) to the wafer (100). Other methods may be used to fix the probe (120) to the wafer (100), such as electrostatic attraction or adhesives.

Figure 3:
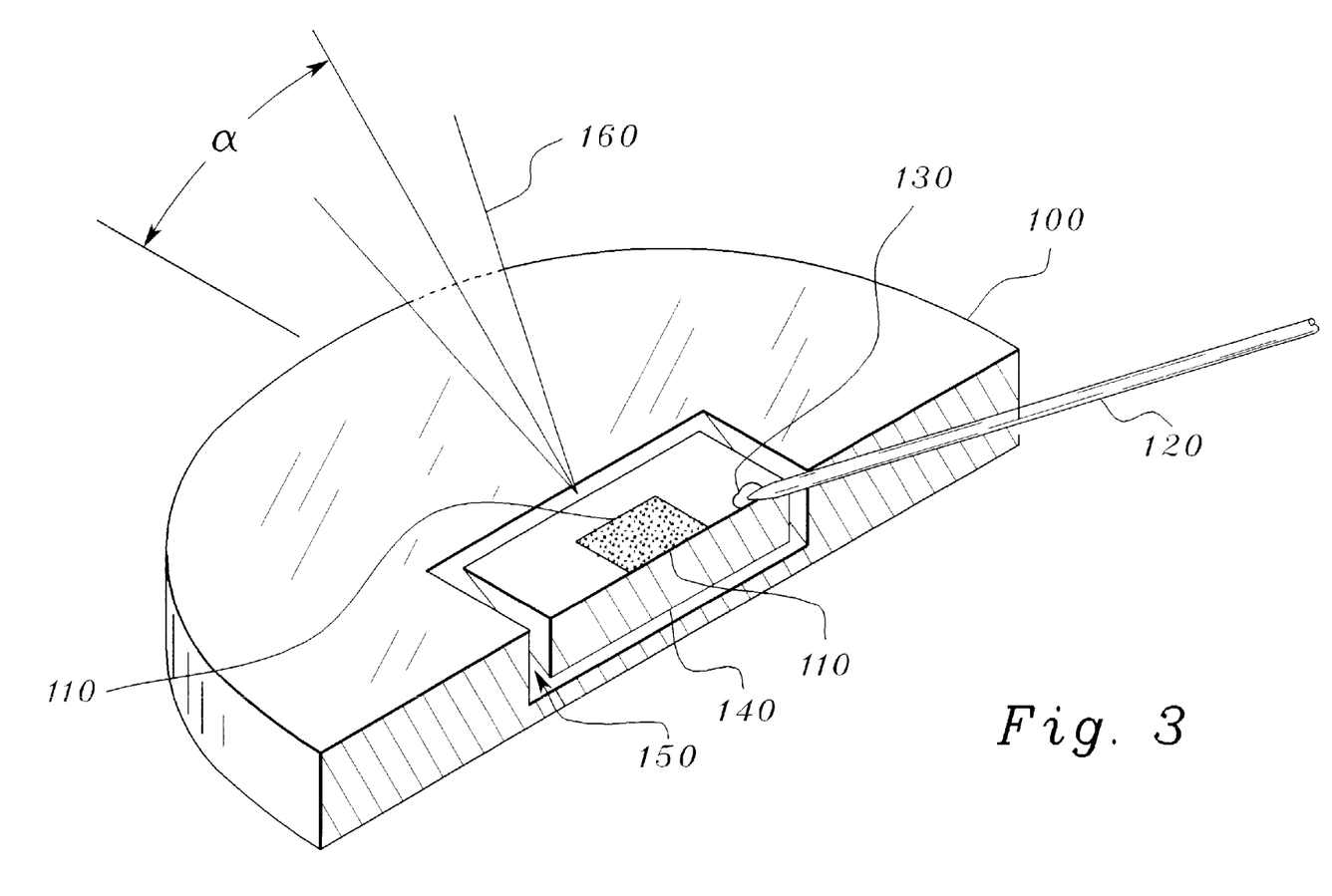
FIG. 3 shows the FIB cutting out a sample bearing the area of interest, or target.

Next, the operator uses the layout functions of the FIB instrument to specify a pattern on the wafer (100) surrounding the target (110), and preferably extending to the edge (115) of the wafer (100) in the y-direction, as shown in FIG. 3. The pattern is preferably U-shaped around the target (110), although a rectangular area, or an arbitrary shape enclosing the target (110) could also be used. This area defines the sample area to be milled by the ion-beam (160). The milling cut (150) should be as thick as necessary to prevent redeposited material from filling the cut. This will depend on the properties of the wafer (100). The specified pattern is milled to completely cut out the sample (140). Gas-assisted etching may also be used, if desired. This operation is illustrated in FIG. 3.

Figure 4:
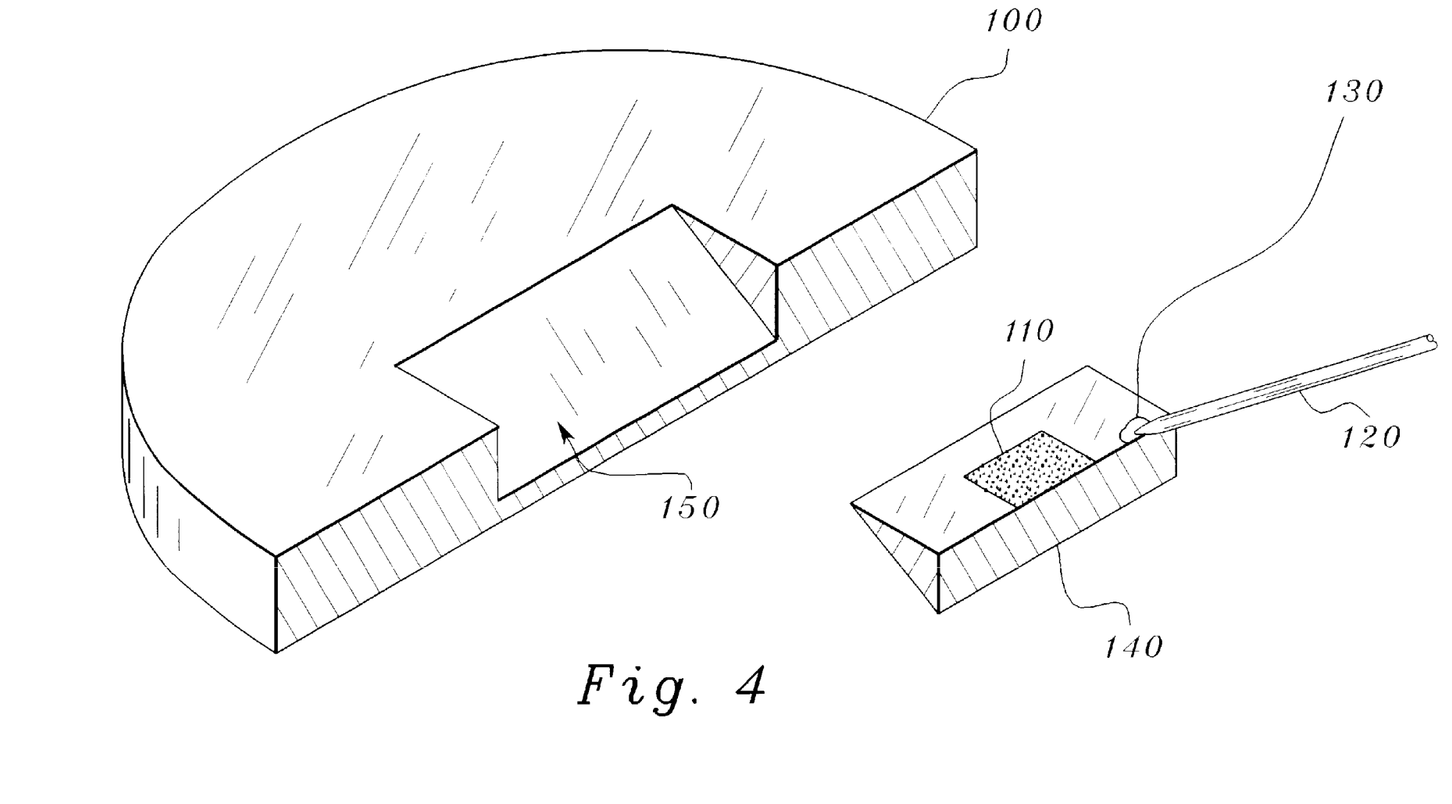
FIG. 4 shows removal of the sample from the wafer.

By viewing the image as the operation proceeds, it will be possible to see when the sample (140) is completely detached. After the sample (140) is completely cut from the wafer (100), the operator will increase the distance between the probe (120) (now holding the sample (140) and target (110)), and the remaining wafer (100), preferably by lowering the FIB stage height by at least 5–10 μm to drop the wafer (100). The operator withdraws the probe (120) holding the target (110) so the sample (140) will be clear of any obstacles when the wafer (100) is exchanged for the TEM grid (200). This operation is shown in FIG. 4. Of course, the sample holder need not be a TEM grid (200) as shown, but may be another type of holder or device suitable for the intended inspection.

When the probe (120) and the sample (140) are completely clear of any potential obstruction, the operator removes the wafer (100) to exchange it for the TEM grid (200) holder. Separation of the cut sample (140) from the wafer (100) is preferably assisted by slightly lowering the wafer (100); typically by lowering the stage in the FIB instrument.

The TEM grid (200) is a standard grid, such as an uncoated 100 or 200 square mesh Cu grid. For the purposes of the method disclosed, the TEM grid (200) is cut across so that the cut bars form "V's" open above (in the z-axis) (see FIG. 5). Using the probe (120) the TEM grid (200) is mounted in the FIB with the cut side up, or with its plane parallel to the z-axis. When the TEM grid (200) is inserted into the FIB, the eucentric position should be set on the cut edge of the TEM grid (200).

Figure 5:
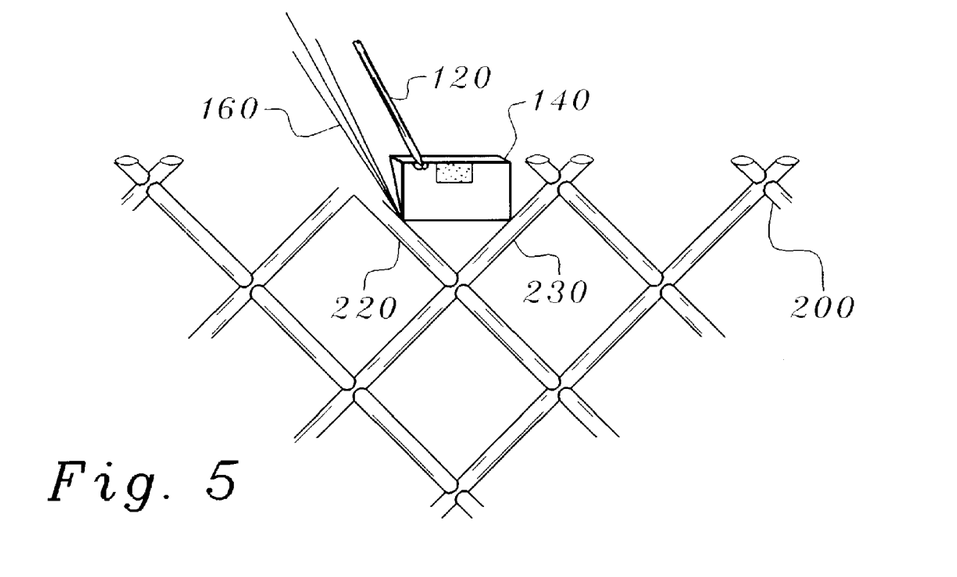
FIGS. 5, 6, 7, and 8 show the attachment of the sample to a TEM grid, and detachment of the probe.
Figure 6:
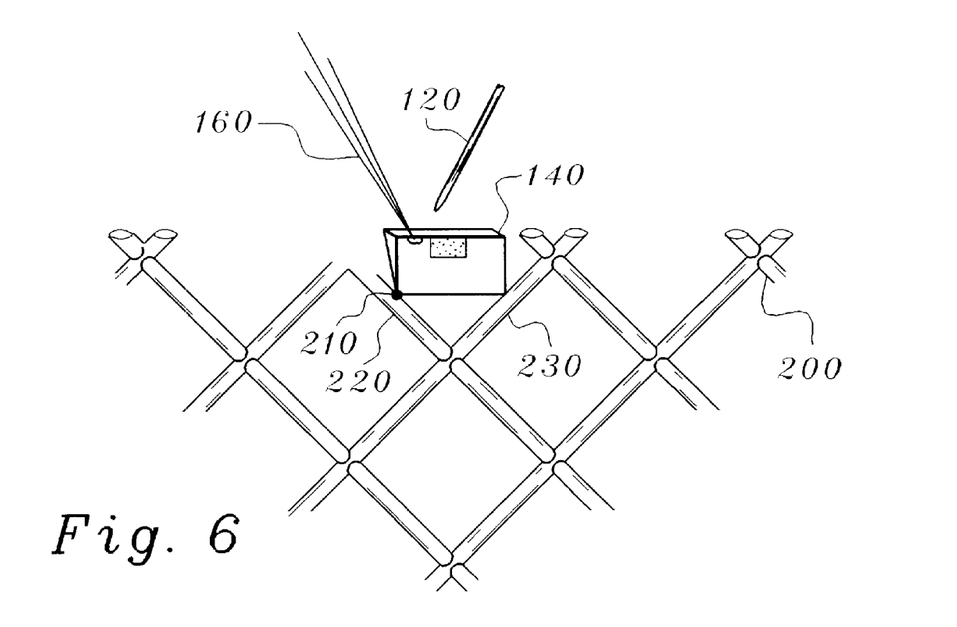
Figure 7:
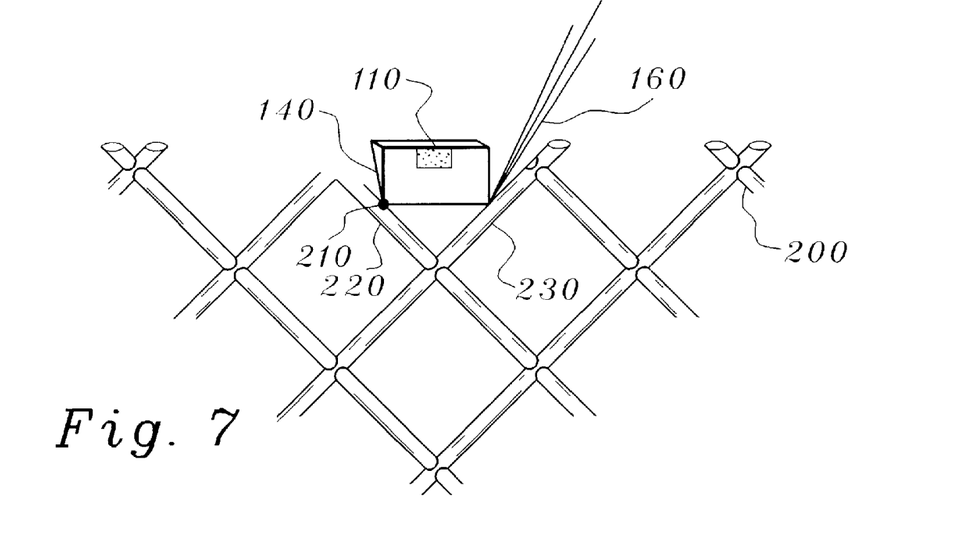
Figure 8:
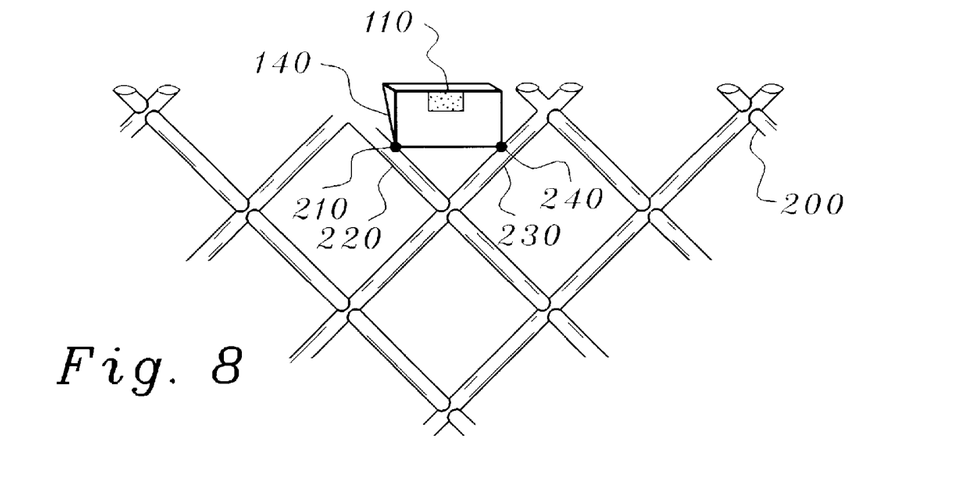

The operator then moves the probe (120) with the sample (140) attached as shown in FIG. 5. The probe (120) is moved until both ends of the sample (140) contact the bars of the TEM grid (200) as shown in FIG. 5 and the following figures. Using FIB metal deposition, the operator welds a free edge of the sample (140) to a first bar (220) of the TEM grid (200) forming a first weld (210). The operator should choose an edge which will allow the ion beam (160) to contact the location of the first weld (210) without interference of the probe (120). FIG. 6 shows the probe (120) detached from the sample weld (130) by use of the ion beam (160). The probe (120) may now be retracted. The operator then uses FIB metal deposition to weld the newly freed edge of sample (140) to a second bar (230) of the TEM grid (200), forming a second weld (240), as shown in FIGS. 7 and 8. The sample can now be thinned by the FIB to a thickness suitable for the TEM application.

In another embodiment of the invention, the method may be used generally to remove a portion of a wafer (considered generally). The probe is attached as described above to the sample of the wafer desired to be removed. Then, the ion beam is positioned to make a single cut that releases the sample. The sample is held attached to the probe, which may be moved away from the wafer and inspected or simply disposed of, if the object is to shape the remaining portion of the wafer. Thus the method is applicable to such applications as micromachining or fabrication of atomic-force microscope tips.

Since those skilled in the art can modify the specific embodiments described above, we intend that the claims be interpreted to cover such modifications and equivalents.

We claim:

1. A method for sample separation and lift-out comprising the steps of:
   a. positioning a wafer, the wafer having a target, inside a FIB instrument, for inspection of the target;
   b. fixing the tip of a probe to the wafer;
   c. Positioning an ion beam at an angle less than 90 degrees to the plane of the wafer;
   d. cutting from one direction with the ion beam a sample of the wafer enclosing the target and the fixed probe, so that the sample is completely released from the wafer;
   e. moving the probe with the sample fixed to it to a holder for inspection;
   f. fixing the sample to the holder; and,
   g. detaching the probe from the sample.

2. The method for sample separation and lift-out of claim 1, where the wafer is first cleaved so as to place the target near the edge of the cleaved wafer.

3. The method for sample separation and lift-out of claim 1, where the probe tip is fixed to the wafer with ion-beam metal deposition.

4. The method for sample separation and lift-out of claim 1, where the probe tip is fixed to the wafer by electrostatic attraction.

5. The method for sample separation and lift-out of claim 1, where the probe tip is fixed to the wafer with adhesive.

6. The method for sample separation and lift-out of claim 1, where the angle of the ion beam with respect to the plane of the wafer is approximately 50 degrees.

7. The method for sample separation and lift-out of claim 1, where the cutting of the ion beam follows a rectangular path on the surface of the wafer; the path surrounding the target and the fixed probe.

8. The method for sample separation and lift-out of claim 1, where the cutting of the ion beam follows a U-shaped path on the surface of the wafer; the path surrounding the target and the fixed probe.

9. The method for sample separation and lift-out of claim 1 where the release of the sample from the wafer is assisted by first lowering the wafer.

10. The method for sample separation and lift-out of claim 1, where the holder is a TEM grid.

11. The method for sample separation and lift-out of claim 1, where the probe is fixed to the holder by ion-beam metal deposition.

12. The method for sample separation and lift-out of claim 1, where the probe is detached from the sample by cutting with the ion beam.

13. The method for sample separation and lift-out of claim 1, where the wafer is a semiconductor device.

14. The method for sample separation and lift-out of claim 1, where the wafer is a micromechanical device.

15. The method for sample separation and lift-out of claim 1, where the effects of the ion beam are assisted by gas-assisted etching.

16. A method for sample separation and lift-out comprising the steps of:
  a. cleaving a wafer, the wafer having a target, so as to place the target near the edge of the cleaved wafer;
  b. fixing the tip of a probe to the wafer by ion-beam metal deposition;
  c. positioning an ion-beam at an angle of approximately 50 degrees to the plane of the wafer;
  d. cutting from one direction with the ion-beam a U-shaped path on the surface of the wafer, the path surrounding the target and the fixed probe, so that the sample is completely released from the wafer;
  e. lowering the wafer slightly;
  f. moving the probe with the sample fixed to it to a TEM grid; the TEM grid having a cut across it to provide a V-shape open above;
  g. fixing the sample to the TEM grid by ion-beam metal deposition; and,
  h. detaching the probe from the sample by cutting with the ion beam.

* * * * *